United States Patent
Kemp et al.

(10) Patent No.: US 9,075,046 B2
(45) Date of Patent: Jul. 7, 2015

(54) FLUIDIC MEDICAL DEVICES AND USES THEREOF

(75) Inventors: Timothy M. Kemp, San Jose, CA (US); Chris Todd, San Jose, CA (US); Ron Oral, Fremont, CA (US); Shulin Zeng, Gaithersburg, MD (US); John Howard, Saratoga, CA (US); Jeff Fenton, San Jose, CA (US)

(73) Assignee: Theranos, Inc., Palo Alto, CA (US)

( * ) Notice: Subject to any disclaimer, the term of this patent is extended or adjusted under 35 U.S.C. 154(b) by 1248 days.

(21) Appl. No.: 12/625,430

(22) Filed: Nov. 24, 2009

(65) Prior Publication Data
US 2010/0074799 A1    Mar. 25, 2010

Related U.S. Application Data

(63) Continuation of application No. 11/388,723, filed on Mar. 24, 2006, now abandoned.

(60) Provisional application No. 60/678,801, filed on May 9, 2005, provisional application No. 60/705,489, filed on Aug. 5, 2005, provisional application No. 60/717,192, filed on Sep. 16, 2005, provisional application No. 60/721,097, filed on Sep. 28, 2005.

(51) Int. Cl.
*G01N 21/75* (2006.01)
*G01N 33/53* (2006.01)
(Continued)

(52) U.S. Cl.
CPC ......... *G01N 33/53* (2013.01); *B01L 2300/0816* (2013.01); *B01L 2300/087* (2013.01); *B01L 2300/021* (2013.01); *B01L 2300/023* (2013.01); *B01L 2300/0887* (2013.01); *B01L 2300/044* (2013.01); *B01L 2300/0867* (2013.01); *B01L 2300/0636* (2013.01); *B01L 2300/0883* (2013.01); *B01L 2300/0877* (2013.01); *B01L 3/50273* (2013.01); *G01N 33/5302* (2013.01); *Y10T 436/115831* (2015.01); *Y10T 436/143333* (2015.01); *Y10T 436/12* (2015.01);
(Continued)

(58) Field of Classification Search
USPC ................ 422/402–404, 408, 417, 420, 430, 422/502–504, 50, 68.1, 82.05–82.09
See application file for complete search history.

(56) References Cited

U.S. PATENT DOCUMENTS

| 4,003,379 A | 1/1977 | Ellinwood |
| 4,146,029 A | 3/1979 | Ellinwood |

(Continued)

FOREIGN PATENT DOCUMENTS

| CN | 2559986 | 7/2003 |
| EP | 1498067 A1 | 1/2005 |

(Continued)

OTHER PUBLICATIONS

European search report and search opinion dated May 29, 2012 for EP Application No. 11180769.9.

(Continued)

*Primary Examiner* — Brian R Gordon

(57) ABSTRACT

This invention is in the field of medical devices. Specifically, the present invention provides fluidic systems having a plurality of reaction sites surrounded by optical barriers to reduce the amount of optical cross-talk between signals detected from various reaction sites. The invention also provides a method of manufacturing fluidic systems and methods of using the systems.

17 Claims, 13 Drawing Sheets

(51) Int. Cl.
*B01L 3/00* (2006.01)
*A61B 5/15* (2006.01)
*A61B 5/145* (2006.01)
*A61B 5/00* (2006.01)
*G01N 33/50* (2006.01)
*A61B 5/155* (2006.01)
*G06F 19/00* (2011.01)
*A61B 5/151* (2006.01)
*A61B 5/157* (2006.01)
*A61B 5/1495* (2006.01)

(52) U.S. Cl.
CPC ............. *Y10T 436/11* (2015.01); *Y10T 436/10* (2015.01); *A61B 5/1411* (2013.01); *A61B 5/14532* (2013.01); *A61B 5/412* (2013.01); *A61B 5/417* (2013.01); *G01N 33/50* (2013.01); *A61B 5/1427* (2013.01); *A61B 5/14546* (2013.01); *A61B 5/1495* (2013.01); *G06F 19/3406* (2013.01); *A61B 5/150022* (2013.01); *A61B 5/150099* (2013.01); *A61B 5/150251* (2013.01); *A61B 5/150854* (2013.01); *A61B 5/15142* (2013.01); *A61B 5/157* (2013.01); *G01N 2500/00* (2013.01)

(56) References Cited

U.S. PATENT DOCUMENTS

| | | | |
|---|---|---|---|
| 4,347,176 A | 8/1982 | Mehta | |
| 4,731,726 A | 3/1988 | Allen | |
| 4,793,825 A | 12/1988 | Benjamin et al. | |
| 4,910,131 A | 3/1990 | Mellman et al. | |
| 4,920,213 A | 4/1990 | Dale et al. | |
| 4,946,795 A | 8/1990 | Gibbons et al. | |
| 5,039,617 A * | 8/1991 | McDonald et al. | 436/69 |
| 5,089,229 A | 2/1992 | Heidt et al. | |
| 5,104,813 A | 4/1992 | Besemer et al. | |
| 5,162,237 A | 11/1992 | Messenger et al. | |
| 5,204,525 A * | 4/1993 | Hillman et al. | 250/252.1 |
| 5,279,607 A | 1/1994 | Schentag et al. | |
| 5,281,395 A | 1/1994 | Markart et al. | |
| 5,380,487 A | 1/1995 | Choperena et al. | |
| 5,443,790 A | 8/1995 | Coeurveille et al. | |
| 5,472,603 A | 12/1995 | Schembri | |
| 5,554,539 A | 9/1996 | Chadney et al. | |
| 5,578,269 A | 11/1996 | Yaremko et al. | |
| 5,624,850 A | 4/1997 | Kumar et al. | |
| 5,670,375 A | 9/1997 | Seaton et al. | |
| 5,674,698 A | 10/1997 | Zarling et al. | |
| 5,716,852 A | 2/1998 | Yager et al. | |
| 5,744,366 A | 4/1998 | Kricka et al. | |
| 5,797,898 A | 8/1998 | Santini et al. | |
| 5,801,057 A | 9/1998 | Smart et al. | |
| 5,807,375 A | 9/1998 | Gross et al. | |
| 5,820,548 A | 10/1998 | Sieben et al. | |
| 5,832,296 A | 11/1998 | Wang et al. | |
| 5,842,787 A | 12/1998 | Kopf-Sill et al. | |
| 5,848,991 A | 12/1998 | Gross et al. | |
| 5,874,214 A | 2/1999 | Nova et al. | |
| 5,885,470 A | 3/1999 | Parce et al. | |
| 5,902,549 A | 5/1999 | Mimura et al. | |
| 5,942,443 A | 8/1999 | Parce et al. | |
| 5,961,451 A | 10/1999 | Reber et al. | |
| 5,961,923 A | 10/1999 | Nova et al. | |
| 5,976,896 A | 11/1999 | Kumar et al. | |
| 5,980,830 A | 11/1999 | Savage et al. | |
| 6,046,056 A | 4/2000 | Parce et al. | |
| 6,074,616 A | 6/2000 | Buechler et al. | |
| 6,123,861 A | 9/2000 | Santini et al. | |
| 6,156,181 A | 12/2000 | Parce et al. | |
| 6,174,675 B1 | 1/2001 | Chow et al. | |
| 6,176,962 B1 | 1/2001 | Soane et al. | |
| 6,200,814 B1 | 3/2001 | Malmqvist et al. | |
| 6,204,068 B1 | 3/2001 | Soini et al. | |
| 6,221,677 B1 | 4/2001 | Wu et al. | |
| 6,245,057 B1 | 6/2001 | Sieben et al. | |
| 6,267,858 B1 * | 7/2001 | Parce et al. | 204/600 |
| 6,299,839 B1 | 10/2001 | Karunaratne et al. | |
| 6,319,668 B1 | 11/2001 | Nova et al. | |
| 6,340,588 B1 | 1/2002 | Nova et al. | |
| 6,352,854 B1 | 3/2002 | Nova et al. | |
| 6,361,958 B1 * | 3/2002 | Shieh et al. | 435/7.1 |
| 6,368,275 B1 | 4/2002 | Sliwa et al. | |
| 6,372,428 B1 | 4/2002 | Nova et al. | |
| 6,375,469 B1 | 4/2002 | Brown | |
| 6,429,025 B1 | 8/2002 | Parce et al. | |
| 6,440,725 B1 | 8/2002 | Pourahmadi et al. | |
| 6,464,687 B1 | 10/2002 | Ishikawa et al. | |
| 6,482,593 B2 | 11/2002 | Walt | |
| 6,491,666 B1 | 12/2002 | Santini, Jr. et al. | |
| 6,503,231 B1 | 1/2003 | Prausnitz et al. | |
| 6,527,762 B1 | 3/2003 | Santini et al. | |
| 6,542,717 B1 | 4/2003 | Zimmerman et al. | |
| 6,544,732 B1 | 4/2003 | Chee et al. | |
| 6,551,838 B2 | 4/2003 | Santini et al. | |
| 6,591,124 B2 | 7/2003 | Sherman et al. | |
| 6,632,216 B2 | 10/2003 | Houzego et al. | |
| 6,649,358 B1 | 11/2003 | Parce et al. | |
| 6,663,003 B2 | 12/2003 | Johnson et al. | |
| 6,703,205 B2 * | 3/2004 | Kopf-Sill et al. | 435/6.19 |
| 6,743,399 B1 * | 6/2004 | Weigl et al. | 422/504 |
| 6,789,510 B1 | 9/2004 | Lee | |
| 6,832,296 B2 | 12/2004 | Hooker | |
| 6,849,237 B2 | 2/2005 | Housefield et al. | |
| 6,858,185 B1 * | 2/2005 | Kopf-Sill et al. | 422/504 |
| 6,878,755 B2 | 4/2005 | Singh et al. | |
| 6,887,202 B2 | 5/2005 | Currie et al. | |
| 6,915,679 B2 * | 7/2005 | Chien et al. | 73/54.01 |
| 6,923,764 B2 | 8/2005 | Aceti et al. | |
| 6,927,851 B2 | 8/2005 | McCaffrey et al. | |
| 6,929,636 B1 | 8/2005 | Von Alten | |
| 6,942,771 B1 * | 9/2005 | Kayyem | 204/409 |
| 6,949,377 B2 | 9/2005 | Ho | |
| 6,966,880 B2 | 11/2005 | Boecker et al. | |
| 7,039,453 B2 | 5/2006 | Mullick et al. | |
| 7,052,831 B2 | 5/2006 | Fletcher et al. | |
| 7,105,183 B2 | 9/2006 | McGrath | |
| 7,112,444 B2 | 9/2006 | Beebe et al. | |
| 7,178,386 B1 | 2/2007 | Gamble et al. | |
| 7,201,872 B2 | 4/2007 | Meron | |
| 7,238,323 B2 * | 7/2007 | Knapp et al. | 422/68.1 |
| 7,291,497 B2 | 11/2007 | Holmes et al. | |
| 7,459,305 B2 | 12/2008 | Levy | |
| 7,497,997 B2 * | 3/2009 | Glezer et al. | 422/504 |
| 7,635,594 B2 | 12/2009 | Holmes et al. | |
| 7,636,667 B2 | 12/2009 | Brown | |
| 7,807,197 B2 | 10/2010 | Lee et al. | |
| 8,055,329 B2 | 11/2011 | Kimchy et al. | |
| 8,202,492 B2 * | 6/2012 | Linder et al. | 422/503 |
| 8,263,006 B2 * | 9/2012 | Sutherland et al. | 422/129 |
| 8,318,109 B2 * | 11/2012 | Saltsman et al. | 422/502 |
| 8,323,887 B2 * | 12/2012 | Webster et al. | 435/6.1 |
| 8,889,083 B2 * | 11/2014 | Ismagilov et al. | 422/502 |
| 2001/0019831 A1 | 9/2001 | Phillips et al. | |
| 2001/0051340 A1 | 12/2001 | Singh et al. | |
| 2001/0051766 A1 | 12/2001 | Gazdzinski | |
| 2001/0053535 A1 | 12/2001 | Bashir et al. | |
| 2002/0001854 A1 | 1/2002 | Lee | |
| 2002/0034757 A1 | 3/2002 | Cubicciotti | |
| 2002/0055094 A1 | 5/2002 | Reece et al. | |
| 2002/0055127 A1 | 5/2002 | Gindilis | |
| 2002/0072733 A1 | 6/2002 | Flaherty | |
| 2002/0092770 A1 | 7/2002 | Hedberg et al. | |
| 2002/0110496 A1 | 8/2002 | Samsoondar | |
| 2002/0114739 A1 | 8/2002 | Weigl et al. | |
| 2002/0120187 A1 | 8/2002 | Eiffert et al. | |
| 2002/0132226 A1 | 9/2002 | Nair et al. | |
| 2002/0143437 A1 | 10/2002 | Handique et al. | |
| 2003/0014362 A1 | 1/2003 | Yim | |
| 2003/0017467 A1 * | 1/2003 | Hooper et al. | 435/6 |
| 2003/0049833 A1 | 3/2003 | Chen et al. | |
| 2003/0049865 A1 | 3/2003 | Santini, Jr. et al. | |
| 2003/0061687 A1 | 4/2003 | Hansen et al. | |

(56) References Cited

U.S. PATENT DOCUMENTS

| | | |
|---|---|---|
| 2003/0069560 A1 | 4/2003 | Adamis et al. |
| 2003/0097092 A1 | 5/2003 | Flaherty |
| 2003/0104590 A1 | 6/2003 | Santini et al. |
| 2003/0117491 A1 | 6/2003 | Avni et al. |
| 2003/0143551 A1 | 7/2003 | Cattell |
| 2003/0148362 A1 | 8/2003 | Luka |
| 2003/0153900 A1 | 8/2003 | Aceti et al. |
| 2003/0167000 A1 | 9/2003 | Mullick et al. |
| 2003/0185706 A1 | 10/2003 | Ribi |
| 2003/0191430 A1 | 10/2003 | D'Andrea et al. |
| 2003/0208113 A1 | 11/2003 | Mault et al. |
| 2003/0208133 A1 | 11/2003 | Mault |
| 2003/0210607 A1 | 11/2003 | Gilbert et al. |
| 2003/0211007 A1 | 11/2003 | Maus et al. |
| 2003/0211618 A1 | 11/2003 | Patel |
| 2003/0214057 A1 | 11/2003 | Huang |
| 2004/0005247 A1 | 1/2004 | Karp |
| 2004/0005582 A1 | 1/2004 | Shipwash |
| 2004/0014202 A1 | 1/2004 | King et al. |
| 2004/0033553 A1 | 2/2004 | Littarru et al. |
| 2004/0047767 A1* | 3/2004 | Bergman et al. ............ 422/99 |
| 2004/0053290 A1 | 3/2004 | Terbrueggen et al. |
| 2004/0086872 A1 | 5/2004 | Childers et al. |
| 2004/0096959 A1 | 5/2004 | Stiene et al. |
| 2004/0109793 A1 | 6/2004 | McNeely et al. |
| 2004/0121305 A1 | 6/2004 | Wiegand et al. |
| 2004/0122486 A1 | 6/2004 | Stahmann et al. |
| 2004/0213825 A1 | 10/2004 | Levy |
| 2004/0228766 A1 | 11/2004 | Witty et al. |
| 2004/0260204 A1 | 12/2004 | Boecker et al. |
| 2005/0009101 A1 | 1/2005 | Blackburn |
| 2005/0019836 A1 | 1/2005 | Vogel et al. |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1 | 5/2005 | Holmes |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | McDevitt et al. |
| 2005/0137481 A1 | 6/2005 | Sheard et al. |
| 2005/0147559 A1 | 7/2005 | Von Alten |
| 2005/0180891 A1* | 8/2005 | Webster et al. ............ 422/100 |
| 2005/0201892 A1* | 9/2005 | Taguchi et al. ............ 422/57 |
| 2005/0209565 A1 | 9/2005 | Yuzhakov et al. |
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2006/0019319 A1 | 1/2006 | Billadeau et al. |
| 2006/0029924 A1 | 2/2006 | Brewster et al. |
| 2006/0062852 A1 | 3/2006 | Holmes |
| 2006/0078998 A1 | 4/2006 | Puskas et al. |
| 2006/0106316 A1 | 5/2006 | Palti |
| 2006/0177873 A1 | 8/2006 | Dowd et al. |
| 2006/0182738 A1 | 8/2006 | Holmes |
| 2006/0211933 A1 | 9/2006 | Zimmermann et al. |
| 2006/0257941 A1 | 11/2006 | McDevitt et al. |
| 2006/0264779 A1 | 11/2006 | Kemp et al. |
| 2006/0264780 A1 | 11/2006 | Holmes et al. |
| 2006/0264781 A1 | 11/2006 | Gibbons et al. |
| 2006/0264782 A1 | 11/2006 | Holmes et al. |
| 2006/0264783 A1 | 11/2006 | Holmes et al. |
| 2007/0059196 A1 | 3/2007 | Brister et al. |
| 2007/0166195 A1 | 7/2007 | Padmanabhan et al. |
| 2007/0224084 A1 | 9/2007 | Holmes et al. |
| 2007/0264629 A1 | 11/2007 | Holmes et al. |
| 2008/0009766 A1 | 1/2008 | Holmes et al. |
| 2008/0113391 A1 | 5/2008 | Gibbons et al. |
| 2010/0081144 A1 | 4/2010 | Holmes et al. |
| 2010/0248277 A1 | 9/2010 | Gibbons et al. |
| 2011/0003699 A1 | 1/2011 | Yoder et al. |
| 2011/0104826 A1 | 5/2011 | Gibbons et al. |
| 2011/0166553 A1 | 7/2011 | Holmes et al. |

FOREIGN PATENT DOCUMENTS

| | | |
|---|---|---|
| JP | H07-304799 | 11/1995 |
| JP | 2002-538440 | 8/2000 |
| JP | 2002-511965 | 4/2002 |
| JP | 2004-527825 | 8/2002 |
| JP | 2005-130855 | 5/2005 |
| JP | 2007-187677 | 7/2007 |
| WO | WO 94/01165 A1 | 1/1994 |
| WO | WO 01/35928 A1 | 5/2001 |
| WO | WO 01/64344 A2 | 9/2001 |
| WO | WO 01/64344 A3 | 3/2002 |
| WO | WO 03/066128 A2 | 8/2003 |
| WO | WO 03/066128 A3 | 12/2003 |
| WO | WO 2005/024437 A1 | 3/2005 |
| WO | WO 2005/025413 A2 | 3/2005 |
| WO | WO 2005/031355 A1 | 4/2005 |
| WO | WO 2005/065157 A2 | 7/2005 |
| WO | WO 2005/065538 A2 | 7/2005 |
| WO | WO 2005/065157 A3 | 10/2005 |
| WO | WO 2005/121367 A1 | 12/2005 |
| WO | WO 2007/120904 A2 | 10/2007 |
| WO | WO 2007/120904 A3 | 10/2007 |

OTHER PUBLICATIONS

Office action dated Apr. 4, 2013 for U.S. Appl. No. 12/986,954.
Office action dated Apr. 30, 2013 for U.S. Appl. No. 13/647,325.
Office action dated Feb. 17, 2009 for U.S. Appl. No. 11/202,231.
Office action dated Feb. 22, 2008 for U.S. Appl. No. 11/202,231.
Office action dated Mar. 3, 2011 for U.S. Appl. No. 11/202,206.
Office action dated Mar. 7, 2006 for U.S. Appl. No. 10/937,872.
Office action dated Mar. 16, 2011 for U.S. Appl. No. 11/202,231.
Office action dated Mar. 18, 2008 for U.S. Appl. No. 11/202,206.
Office action dated Mar. 22, 2010 for U.S. Appl. No. 11/202,206.
Office action dated Apr. 18, 2007 for U.S. Appl. No. 10/937,872.
Office action dated Jun. 21, 2007 for U.S. Appl. No. 11/202,231.
Office action dated Jul. 28, 2009 for U.S. Appl. No. 11/202,206.
Office action dated Sep. 1, 2005 for U.S. Appl. No. 10/937,872.
Office action dated Oct. 26, 2006 for U.S. Appl. No. 10/937,872.
Office action dated Nov. 5, 2009 for U.S. Appl. No. 11/202,231.
Office action dated Nov. 22, 2011 for U.S. Appl. No. 11/202,231.
Office action dated Dec. 19, 2008 for U.S. Appl. No. 11/202,206.
U.S. Appl. No. 13/896,171, filed May 16, 2013, Holmes et al.
International search report and written opinion dated Sep. 16, 2008 for PCT/US2007/009878.
Office action dated Jun. 5, 2013 for U.S. Appl. No. 12/750,518.
Office action dated Jun. 24, 2013 for U.S. Appl. No. 13/436,568.
Khan, et al. Detection of influenza virus neuraminidase-specific antibodies by an enzyme-linked immunosorbent assay. J Clin Microbiol. Jul. 1982;16(1):115-22.
Office action dated Sep. 4, 2013 for U.S. Appl. No. 11/388,823.
Office action dated Feb. 1, 2013 for U.S. Appl. No. 13/187,960.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05 (in Japanese with English translation).
Ray, et al. Distinct hemagglutinin and neuraminidase epitopes involved in antigenic variation of recent human parainfluenza virus type 2 isolates. Virus Res. Jun. 1992;24(1):107-13.
U.S. Appl. No. 14/050,235, filed Oct. 9, 2013.
Office action dated Oct. 31, 2013 for U.S. Appl. No. 12/986,954.
European search report dated Feb. 7, 2012 for EP Application No. 11180769.9.
European search report and search opinion dated Mar. 6, 2012 for EP Application No. 10179887.4.
Office action dated Jan. 5, 2010 for U.S. Appl. No. 11/388,415.
Office action dated Jan. 8, 2013 for U.S. Appl. No. 11/388,415.
Office action dated Feb. 2, 2011 for U.S. Appl. No. 11/746,535.
Office action dated Feb. 22, 2008 for U.S. Appl. No. 11/746,535.
Office action dated Feb. 27, 2009 for U.S. Appl. No. 11/388,723.
Office action dated Mar. 5, 2009 for U.S. Appl. No. 11/388,823.
Office action dated Mar. 5, 2010 for U.S. Appl. No. 11/746,535.
Office action dated Mar. 17, 2009 for U.S. Appl. No. 11/388,415.

(56) References Cited

OTHER PUBLICATIONS

Office action dated Mar. 21, 2008 for U.S. Appl. No. 11/388,723.
Office action dated Mar. 21, 2011 for U.S. Appl. No. 11/388,415.
Office action dated Apr. 1, 2010 for U.S. Appl. No. 11/388,824.
Office action dated Apr. 5, 2010 for U.S. Appl. No. 11/554,509.
Office action dated Apr. 8, 2009 for U.S. Appl. No. 11/389,410.
Office action dated Apr. 13, 2012 for U.S. Appl. No. 11/554,509.
Office action dated Apr. 29, 2009 for U.S. Appl. No. 11/389,409.
Office action dated Apr. 30, 2009 for U.S. Appl. No. 11/388,824.
Office action dated May 22, 2009 for U.S. Appl. No. 11/746,535.
Office action dated May 29, 2012 for U.S. Appl. No. 12/986,954.
Office action dated Jun. 1, 2007 for U.S. Appl. No. 11/389,409.
Office action dated Jun. 1, 2012 for U.S. Appl. No. 11/388,823.
Office action dated Jun. 9, 2010 for U.S. Appl. No. 11/746,535.
Office action dated Jun. 11, 2012 for U.S. Appl. No. 11/388,415.
Office action dated Jul. 18, 2012 for U.S. Appl. No. 12/576,197.
Office action dated Jul. 25, 2008 for U.S. Appl. No. 11/389,409.
Office action dated Jul. 27, 2011 for U.S. Appl. No. 11/554,509.
Office action dated Jul. 29, 2011 for U.S. Appl. No. 12/986,954.
Office action dated Aug. 24, 2010 for U.S. Appl. No. 11/388,415.
Office action dated Aug. 27, 2010 for U.S. Appl. No. 11/388,823.
Office action dated Aug. 29, 2008 for U.S. Appl. No. 11/388,823.
Office action dated Aug. 31, 2011 for U.S. Appl. No. 12/221,816.
Office action dated Sep. 5, 2008 for U.S. Appl. No. 11/388,723.
Office action dated Sep. 11, 2008 for U.S. Appl. No. 11/389,409.
Office action dated Sep. 22, 2011 for U.S. Appl. No. 12/576,197.
Office action dated Oct. 6, 2008 for U.S. Appl. No. 11/746,535.
Office action dated Oct. 17, 2008 for U.S. Appl. No. 11/389,410.
Office action dated Nov. 9, 2011 for U.S. Appl. No. 11/388,823.
Office action dated Dec. 11, 2012 for U.S. Appl. No. 12/750,518.
Office action dated Dec. 22, 2009 for U.S. Appl. No. 11/388,823.
Office action dated Dec. 22, 2010 for U.S. Appl. No. 11/554,509.
Lupiani, et al. Improved diagnostic tests for Avian influenza surveillance, 2005. Proceedings of the Institute of Food Technologists' First Annual Forod protection and Defense Research Conference.
Pescovitz, D. Sniffing out airborne diseases. Lab Note: Research from the College of Engineering, University of California, Berkeley, 2004. Available online at http://www.coe.berkeley.edu/labnotes/0904/pisano.html. Accessed Jan. 28, 2011.
Broadcaster Moira Gunn with Elizabeth Homes, recorded Mar. 5, 2005 on Biotech Nation.
Pal, et al. An integrated microfluidic device for influenza and other genetic analyses. Lab Chip. Oct. 2005;5(10):1024-32. Epub Aug. 18, 2005.
Patofsky, et al. Electrical detection of single viruses. Proc Natl Acad Sci U S A. Sep. 28, 2004;101(39):14017-22. Epub Sep. 13, 2004.
Red Herring. Stopping bad reactions. Red Herring. Dec. 26, 2005.
Geddes, et al. The impedance of stainless-steel electrodes. Med Biol Eng. Sep. 1971;9(5):511-21.
Hirsch, et al. The electrical conductivity of blood. I: Relationship to erythrocyte concentration. Blood. Nov. 1950;5(11):1017-35.
Mohapatra, et al. Blood resistivity and its implications for the calculation of cardiac output by the thoracic electrical impedance technique. Intensive Care Med Aug. 1977;3(2):63-7.
Bawendi, et al. The quantum-mechanics of larger semiconductor clusters. Annu. Rev. Phys. Chem. 1990; 41:477-496.
BD Biosciences, Directigen FluA&B Assay Manual. Oct. 11, 2006, pp. 1-11.
Beier, et al. Versatile derivatisation of solid support media for covalent bonding on Dna-microchips. Nucleic Acids Res. 1999; 27:1970-1977.
Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.
Bhatia, et al. Use of thiol-terminal silanes and heterobifunctional crosslinkers for immobilization of antibodies on silica surfaces. Anal Biochem. 1989; 178(2):408-13.
Bruchez, et al. Semiconductor nanocrystals as fluorescent biological labels. Science. 1998; 281(5385):2013-6.

Celebre, et al. A comparative study of efficiencies of fibre optic and prism TIRF sensors. Meas. Sci. Technol. 1992; 3:1166-1173.
Chan. Quantum dot bioconjugates for ultrasensitive nonisotopic detection. Science. 1998; 281(5385):2016-8.
Chang, et al. Micromachining & Microfabrication. SPIE Optical Engineering Press. Bellingham, Wash. 1997. (Cover pages and table of contents only).
Charles, et al. Synthesis of a fluorescent analog of polychlorinated biphenyls for use in a continuous flow immunosensor assay. Bioconjug Chem. 1995; 6(6):691-4.
Duffy, et al. Rapid Prototyping of Microfluidic Systems in Poly(dimethylsiloxane). Analytical Chemistry. 1998; 70(23):4974-4984.
European search report dated Jun. 2, 2009 for Application No. 07762092.
Gavin, et al. Review of Rapid Diagnostic Tests for Influenza. Clinical and Applied.
Immunology Reviews. 2004; 4(3):151-172.
Harlow, et al. Antibodies: A Laboratory Manual. Cold Spring Harbor Laboratory. New York. 1988. (Cover pages and table of contents only).
Harrison's Principles of Internal Medicine, Part 2 Cardinal Manifestations of Disease, Ch. 60 (12th ed. 1991; pp. 338-343.).
International search report date Jan. 22, 2008 for PCT Application No. US06/42563.
International search report date Aug. 11, 2008 for PCT Application No. US07/68665.
International search report date Sep. 9, 2008 for PCT Application No. US07/23904.
International search report date Dec. 8, 2008 for PCT Application No. US06/11090.
International search report dated Jul. 4, 2005 for PCT Application No. US2004/029462.
Jaeger. Introduction to Microelectronic fabrication. Addison-Wesley Pubishing Co. Reading Mass. 1988. (Cover pages and table of contents only).
Kessler, et al. Use of the DNA flow-thru chip, a three-dimensional biochip, for typing and subtyping of influenza viruses. J Clin Microbiol. May 2004;42(5):2173-85.
Lee, et al. Microfluidic enzyme-linked immunosorbent assay technology. Adv Clin Chem. 2006;42:255-95.
Liu, et al. Validation of a fully integrated microfluidic array device for influenza A subtype identification and sequencing. Anal Chem. Jun. 15, 2006;78(12):4184-93.
Mukerjee, et al. Microneedle array for transdermal biological fluid extraction and in situ analysis. Sensors and Actuators A. 2004; 114:267-275.
Preininger, et al. Polymer-coated optical fibres for application in a direct evanescent wave immunoassay. Analytica Chimica Acta, 2000; 403, 67-76.
Rai-Choudhury, ed., Handbook of Microlithography, Micromachining & Microfabrication. SPIE Optical Engineering Press. Bellingham, Wash. 1997. (Cover pages and table of contents only).
Runyan, et at Semiconductor integrated circuit processing technology. Addison-Wesley Publishing Co., Reading Mass. 1990. (Cover pages and table of contents only).
Sambrook, et al. Molecular Cloning: A Laboratory Manual. Cold Spring Harbor Laboratory Press. New York. 2001. (Cover pages and table of contents only).
Sapsford, et al. Demonstration of four immunoassay formats using the array biosensor. Anal Chem. 2002; 74(5):1061-8.
Scheurle, et al. HER-2/neu expression in archival non-smaill cell lung carcinomas using FDA-approved hercep test. Anticancer Res. 2000; 20:2091-2096.
Spira, et al. The identification of monoclonal class switch variants by sib selection and an ELISA assay. J Immunol Methods. 1984;74(2):307-15.
Steplewski, et al. Isolation and characterization of antimonosialoganglioside monoclonal antibody 19-9 class-switch variants. Proc Natl Acad Sci U S A. 1985; 82(24):8653-7.

(56) References Cited

OTHER PUBLICATIONS

Stevens, et al. Glycan microarray analysis of the hemagglutinins from modern and pandemic influenza viruses reveals different receptor specificities. J Mol Biol. Feb. 3, 2006;355(5):1143-55.
Tedeschi, et al. Antibody immobilisation on fibre optic TIRF sensors. Biosens Bioelectron. 2003; 19(2):85-93.

Yan, et al. Multiplexed flow cytometric immunoassay for influenza virus detection and differentiation. Anal Chem. Dec. 1, 2005;77(23):7673-8.
Kilbourne, et al. Independent and disparate evolution in nature of influenza a virus hemagglutinin and neuraminidase glycoproteins. Proc Natl Acad Sci U S A. Jan. 1990;87(2):786-90.

* cited by examiner

FLUIDIC MEDICAL DEVICES AND USES THEREOF

CROSS-REFERENCE

This application is a continuation application of U.S. application Ser. No. 11/388,723, filed Mar. 24, 2006, which is now abandoned, which claims the benefit of U.S. Provisional Application No. 60/678,801, filed May 9, 2005 and U.S. Provisional Application No. 60/705,489, filed Aug. 5, 2005 and U.S. Provisional Application No. 60/717,192, filed Sep. 16, 2005, and U.S. Provisional Application No. 60/721,097, filed Sep. 28, 2005 which are incorporated herein by reference in their entirety.

BACKGROUND OF THE INVENTION

Point-of-Care (POC) testing systems and fluidic devices or cartridges are becoming more common because of the advancement in microfabrication technology such as MEMS technology, which enables the fabrication of reliable and inexpensive fluidic based cartridges. Generally, such systems use microvalves, micropumps, microneedles, etc. for moving the fluids through the fluidic system. A common system contains a reagent reservoir, a mixing chamber, an analytical chamber and waste chamber. Fluids must therefore be moved from one chamber to another. Some challenges in moving such fluids in a fluidic device include mixing the reagents with the sample, and washing unbound reagents from a detection site. One of the common challenges is washing the unbound conjugates after the incubation period, particularly removing conjugates that remain stuck to the edges of the reaction site walls. U.S. Pat. No. 5,600,993 provides a good summary of such exemplary problems.

Various approaches that have been described to cause fluid movement in a fluidic device include electrical, osmotic, and capillary. U.S. Pat. No. 6,440,725 describes different fluid motive sources for moving liquids through the chambers. One such example uses a fluid inside a sealed pouch wherein the fluid is converted to gas by an electrical current. This action pressurizes and expands the fluid pouch. This sealed pumping pouch, or e-pump, is positioned against a reagent pouch and forces the contents of the reagent pouch into the fluidic circuit as the pumping pouch expands. The '725 patent also describes various other fluid motive sources such as pressure or vacuum source, or using a solenoid or stepper motor to provide a force to press against a reagent pouch.

US Patent Application No. 20050130292 describes using mechanical energy to move fluids within a fluidic device. In this application the inventors describe minimal or no external power to force the fluid through various chambers. A sample is loaded on to a biochip and this biochip is inserted into a custom designed socket. The work done in inserting the socket is converted to the energy required for the fluidic flow. Subsequent steps of directing the sample to the desired chamber, mixing it, and assaying it are, according to the inventors, accomplished with minimal power consumption. Such a device has several valves and pumps, even if the pumps are not driven by external electrical energy, which are difficult to include in a small disposable fluidic system.

Generally, reagents in a POC system are stored in a dry state to improve shelf-like. Buffers are generally stored separately until the assay is to be performed, at which time the reagents are hydrated. However, dry reagents may become wet or hydrated before they are intended to do so. Buffers may leak from their holding areas and mix with the dry reagents. It may thus be beneficial to keep the dry reagents in a dry state until the assay is initiated.

Cartridge or fluidic based POC systems may handle small volumes of fluids. Nanoliter or even picoliter amounts of fluids are sometimes forced to flow within fluidic channels. Either during the sample introduction or a venting process, there is a substantial likelihood that a bubble will be introduced into the microfluidics system. A bubble introduced into the system can cause an inaccurate measurement if the bubble is located in the detection site during the detection step.

Current fluidic devices may experience optical cross-talk when there are multiple reaction sites adjacent to one another. When assays with different luminescent intensities are run in adjacent reaction wells or chambers, photons (representing the signal generated) can travel from one well to others comprising the accuracy of measurement from each well. The photons can travel through construction materials of the wells and through the fluidic channels that connect the wells. This problem may become worse the longer the incubation time of the assay. Thus, there remains a considerable need for new designs of fluidic cartridges with reduced optical interference from adjacent reaction sites. The present invention satisfies this need and provides related advantages as well.

SUMMARY OF THE INVENTION

The present invention provides an apparatus for detecting an analyte in a biological fluid of a subject. The apparatus comprises a sample collection unit for introducing a biological fluid in fluid communication with a plurality of reaction sites, a plurality of reactant chambers carrying a plurality of reactants in fluid communication with said reaction sites wherein said plurality of reaction sites comprise a plurality of reactants bound thereto for detecting said analyte, and a system of fluidic channels to allow said biological fluid and said plurality of reactants to flow in said apparatus, wherein at least one channel located between said plurality of reaction sites comprises an optical barrier to reduce the amount of optical cross-talk between said plurality of said reaction sites during detection of said analyte.

In one aspect, the apparatus further comprising a plurality of waste chambers in fluid communication with at least one of said reaction sites. In another aspect, each channel located between said plurality of reaction sites comprises an optical barrier.

The present invention also provides an apparatus for detecting an analyte in a biological fluid of a subject comprises a sample collection unit for introducing a biological fluid in fluid communication with a plurality of reaction sites, wherein said plurality of reaction sites comprise a plurality of bound reactants for detecting said analyte, a plurality of reactant chambers carrying a plurality of reactants in fluid communication with said reaction sites, and a system of fluidic channels to allow said biological fluid and said plurality of reactants to flow in said apparatus wherein said bound reactants in at least one reaction site are unevenly distributed.

The present invention further provides a method of manufacturing a fluidic device for detecting an analyte in a biological fluid of a subject. The method comprises providing a plurality of layers of a fluidic device, and ultrasonically welding said layers together such that a fluidic network exists between a sample collection unit, at least one reactant chamber, at least one reaction site, and at least one waste chamber.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
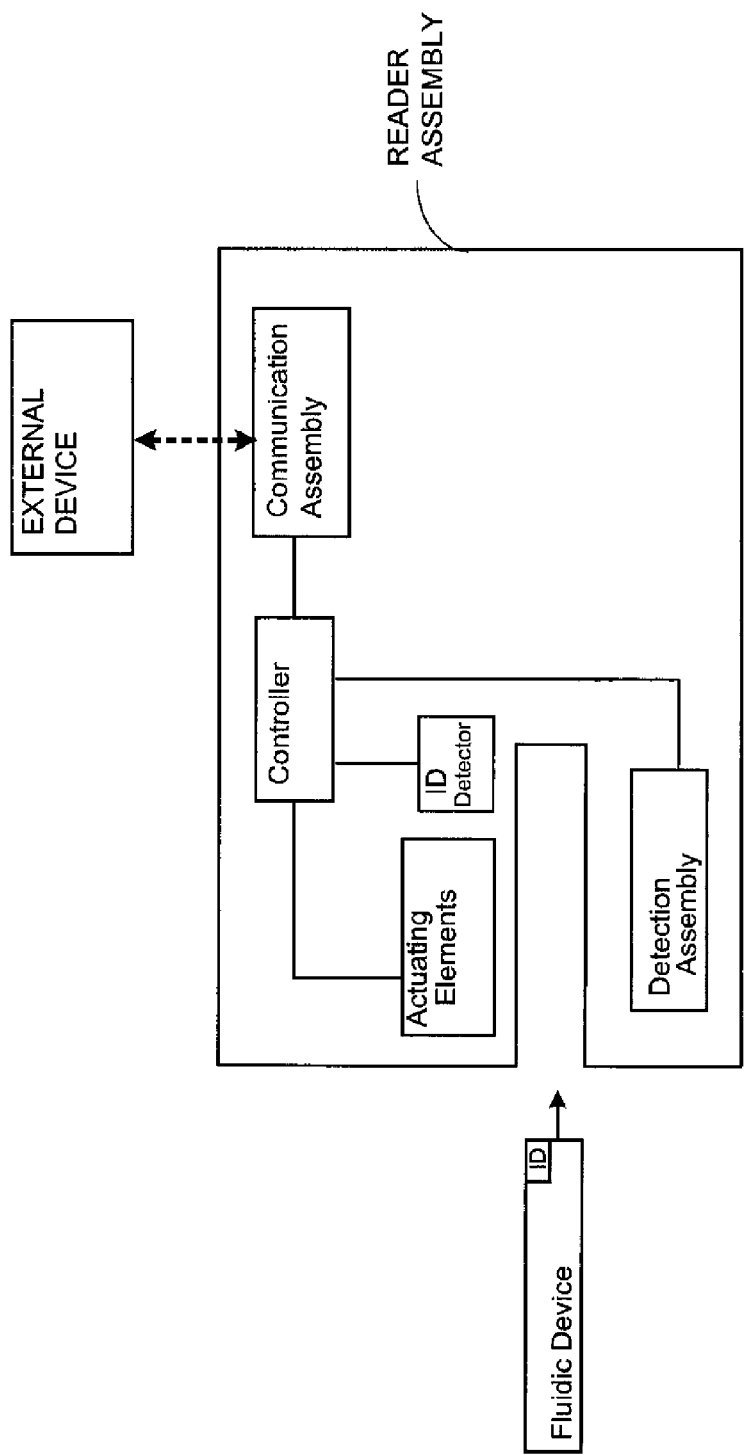
FIG. 1 illustrates exemplary multiple components of the present system.

One aspect of the present invention is a system for detecting an analyte in a sample of bodily fluid. The subject system has one or more of the following components: a) a sample collection unit for introducing a biological fluid in fluid communication with a plurality of reaction sites, b) a plurality of reactant chambers carrying a plurality of reactants in fluid communication with said reaction sites wherein said plurality of reaction sites comprise a plurality of reactants bound thereto for detecting said analyte, and c) a system of fluidic channels to allow said biological fluid and said plurality of reactants to flow in said apparatus, wherein at least one channel located between said plurality of reaction sites comprises an optical barrier to reduce the amount of optical cross-talk between said plurality of said reaction sites during detection of said analyte.

Where desired, the system may further comprise a reader assembly and a communication assembly. The sample collection unit typically allows a sample of bodily fluid collected from a subject to react with reactants contained within the assay assembly for generating a signal indicative of the presence of the analyte of interest. The reader assembly detects the signal, which is then transmitted via the communication assembly to an external device for further processing.

Any bodily fluids suspected to contain an analyte of interest can be used in conjunction with the subject system or devices. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid. In a preferred embodiment, the bodily fluids are used directly for detecting the analytes present therein with the subject fluidic device without further processing. Where desired, however, the bodily fluids can be pre-treated before performing the analysis with the subject fluidic devices. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the analyte is a molecule present on or within a cell, extraction can be performed using lysing agents including but not limited to denaturing detergent such as SDS or non-denaturing detergent such as thesit, sodium deoxylate, triton X-100, and tween-20.

The volume of bodily fluid to be used with a fluidic device of the present invention is generally less than about 500 microliters, typically between about 1 to 100 microliters. Where desired, a sample of 1 to 50 microliters or 1 to 10 microliters can be used for detecting an analyte using the subject fluidic device.

A bodily fluid may be drawn from a patient and brought into the fluidic device in a variety of ways, including but not limited to, lancing, injection, or pipetting. In one embodiment, a lancet punctures the skin and draws the sample into the fluidic device using, for example, gravity, capillary action, aspiration, or vacuum force. The lancet may be part of the fluidic device, or part of a reader assembly, or as a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the fluidic device, as for example, could occur with a saliva sample. The collected fluid can be placed in the sample collection unit within the fluidic device. In yet another embodiment, the fluidic device comprises at least one microneedle which punctures the skin. The microneedle can be used with a fluidic device alone, or can puncture the skin after the fluidic device is inserted into a reader assembly.

In some embodiments a microneedle is about the size of a human hair and has an integrated microreservoir or cuvette. The microneedle may painlessly penetrate the skin and draw a small blood sample. More preferably, the microneedle collects about 0.01 to about 1 microliter, preferably about 0.05 to about 0.5 microliters and more preferably about 0.1 to about 0.3 microliters of capillary blood. In some embodiments a microneedle may be constructed out of silicon and is about 10 to about 200 microns in diameter, preferably about 50 to about 150 microns in diameter, and most preferably about 100 microns in diameter, making their application to the skin virtually painless. To ensure that a capillary is actually struck by a needle, a plurality of microneedles may be used for sample collection. Such microneedles may be of the type marketed by Pelikan (Palo Alto, Calif.) and/or Kumetrix (Union City, Calif.). U.S. Pat. No. 6,503,231 discloses microneedles which may be used with the present invention.

Microfabrication processes that may be used in making the microneedles disclosed herein include without limitation lithography; etching techniques such as wet chemical, dry, and photoresist removal; thermal oxidation of silicon; electroplating and electroless plating; diffusion processes such as boron, phosphorus, arsenic, and antimony diffusion; ion implantation; film deposition such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). Alternatively, microneedles may be molded in silicon wafers and then plated using conventional wire cutting techniques with nickel, gold, titanium or various other biocompatible metals. In some embodiments microneedles can be fashioned from biopolymers. In some embodiments microneedles may be fabricated and employed for the claimed devices according to the methods of Mukerjee et al., Sensors and Actuators A: Physical, Volume 114, Issues 2-3, 1 Sep. 2004, Pages 267-275.

In preferred embodiments a microneedle is only used once and then discarded. In some embodiments a mechanical actuator can insert and withdraw the microneedle from the patient, discard the used needle, and reload a new microneedle. The mechanical technologies developed and manufactured in very high volumes for very small disk drives have a similar set of motion and low cost requirements. In preferred embodiments the actuator is a MEMS (micro machined electromechanical system) device fabricated using semiconductor-like batch processes. Such actuators include without limitation nickel titanium alloy, pneumatic, or piezo electric devices. In some embodiments the microneedles are about 1 micron to about 10 microns in thickness, preferably about 2 microns to about 6 microns in thickness, and most preferably about 4 microns in thickness. In some embodiments the microneedles are about 10 microns to about 100 microns in height, preferably about 30 microns to about 60 microns in height, and most preferably about 40 microns in height.

FIG. 1 illustrates an exemplary system of the present invention. As illustrated, a fluidic device provides a bodily fluid from a patient and can be inserted into a reader assembly. The fluidic device may take a variety of configurations and in some embodiments the fluidic device may be in the form of a cartridge. An identifier (ID) detector may detect an identifier on the fluidic device. The identifier detector communicates with a communication assembly via a controller which transmits the identifier to an external device. Where desired, the external device sends a protocol stored on the external device to the communication assembly based on the identifier. The protocol to be run on the fluidic device may comprise instructions to the controller of the reader assembly to perform the protocol on the fluidic device, including but not limited to a particular assay to be run and a detection method to be performed. Once the assay is performed on the fluidic device, a signal indicative of an analyte in the bodily fluid sample is generated and detected by a detection assembly. The detected signal may then be communicated to the communications assembly, where it can be transmitted to the external device for processing, including without limitation, calculation of the analyte concentration in the sample.

Figure 2:
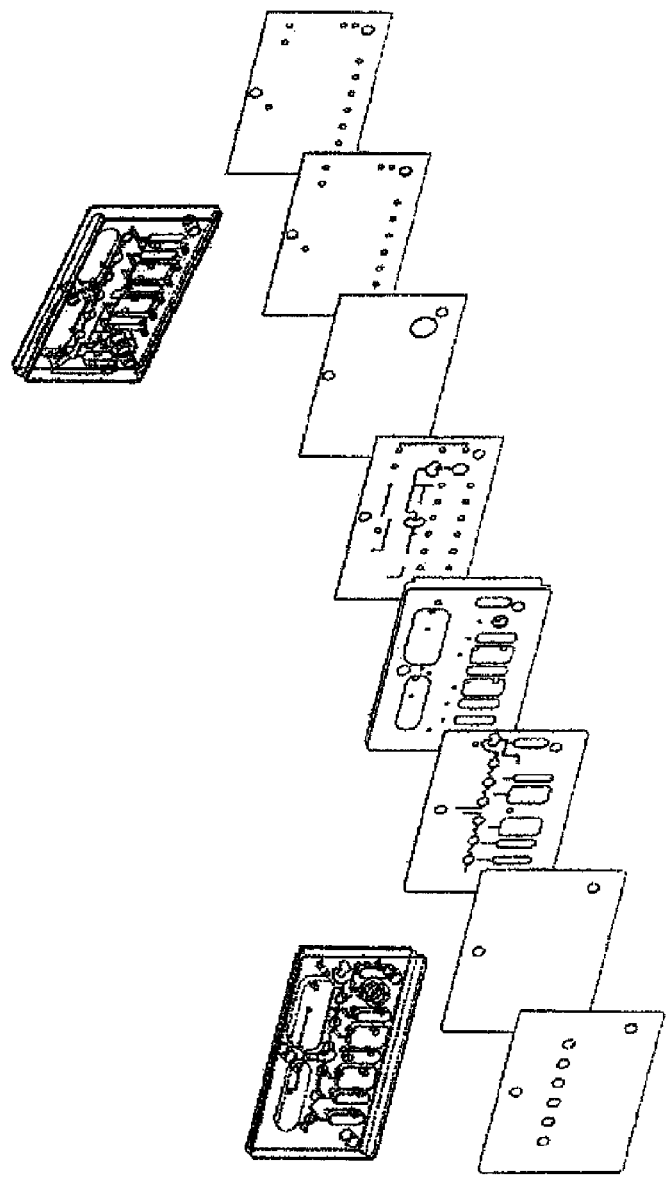
FIG. 2 shows different layers of an exemplary fluidic device prior to assembly.
Figure 3:
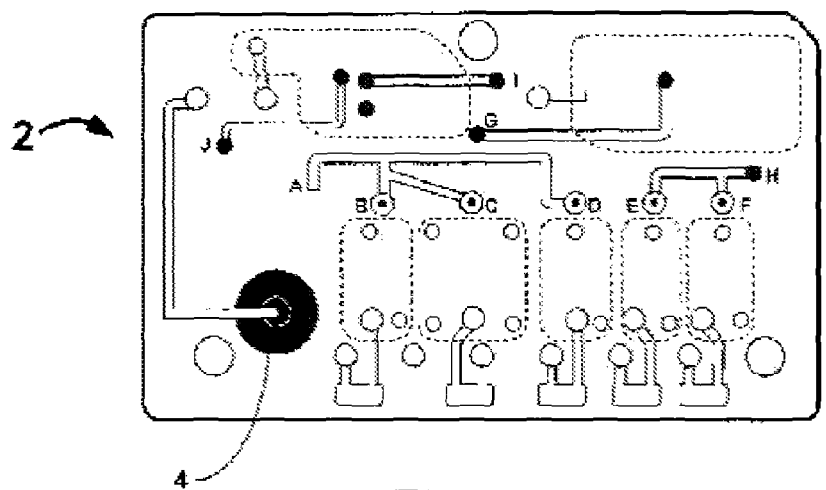
FIGS. 3 and 4 illustrate the fluidic network within an exemplary fluidic device.
Figure 4:
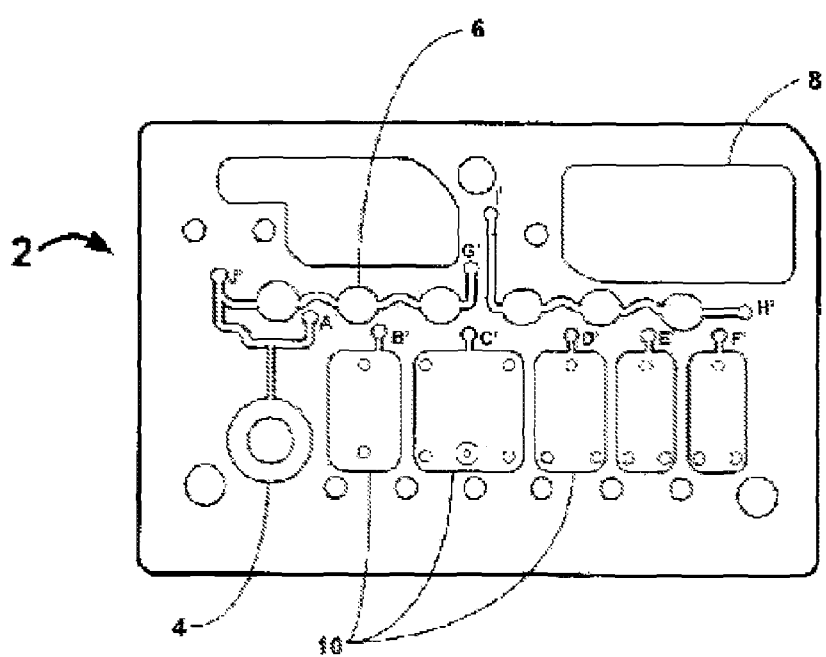

FIG. 2 illustrates exemplary layers of a fluidic device according to the present invention prior to assembly of the fluidic device which is disclosed in more detail below. FIGS. 3 and 4 illustrate the fluidic network within an exemplary fluidic device. The different layers are designed and assembled to form a three dimensional fluidic channel network. A sample collection unit 4 provides a sample of bodily fluid from a patient. As will be explained in further detail below a reader assembly comprises actuating elements (not shown) can actuate the fluidic device to start and direct the flow of a bodily fluid sample and assay reagents in the fluidic device. In some embodiments actuating elements first cause the flow of sample in the fluidic device 2 from sample collection unit 4 to reaction sites 6, move the sample upward in the fluidic device from point G' to point G, and then to waste chamber 8. The actuating elements then initiate the flow of reagents from reagent chambers 10 to point B', point C', and point D', then upward to points B, C, and D, respectively. The reagents then move to point A, down to point A', and then to waste chamber 8 in a manner similar to the sample.

A sample collection unit 4 in a fluidic device 2 may provide a bodily fluid sample from a patient by any of the methods described above. If necessary, the sample may first be processed by diluting the bodily fluid in a dilution chamber, and or may be filtered by separating the plasma from the red blood cells in a filtration chamber. In some embodiments the sample collection unit, diluting chamber, and filtration chamber may be the same component, and in some embodiments they may be different components, or any two may be the same component and the other may be a separate component. In some embodiments there may be more than one sample collection unit in the fluidic device.

In some embodiments it may be desirable to detect the presence of analytes on a cell surface, within a cell membrane, or inside a cell. The difficulty of detecting such analytes is that cells and other formed elements are particulate and components of cells do not readily interact with traditional assay chemistries which are designed to operate on analytes in solution. Cell-surface analytes react slowly and inefficiently with surface bound probes, and analytes inside the cell can not react at all with bound probes. To allow the detection of such analytes, in some embodiments the fluidic device may include a lysing assembly to lyse cells present in the bodily fluid sample. The lysing assembly may be incorporated with the sample collection unit, a dilution chamber, and/or a filtration chamber. In some embodiments the sample collection unit, dilution chamber, and lysing component are within the same element in the fluidic device. In some embodiments the lysing component may be incorporated with an assay reagent described below.

Where desired, lysing agents may be impregnated and then dried into porous mats, glass fiber mats, sintered frits or particles such as Porex, paper, or other similar material. Lysing agents may be dried onto flat surfaces. Lysing agents may also be dissolved in liquid diluents or other liquid reagents. In preferred embodiments porous materials are used to store the lysing agents because they can store a lysing agent in dry form likely to be very stable. They also facilitate the mixing of the bodily fluid sample with the lysing agent by providing a tortuous path for the sample as it moves through the porous material. In preferred embodiments such porous materials have a disc shape with a diameter greater than its thickness. In some embodiments lysing agents may be dried onto porous materials using lyophilization, passive evaporation, exposure to warm dry flowing gas, or other known methods.

A variety of lysing agents are available in the art and are suitable for use in connection with the subject fluidic device. Preferred lysing agents are non-denaturing, such as non-denaturing detergents. Non-limiting examples of non-denaturing detergents include thesit, sodium deoxylate, triton X-100, and tween-20. The agents are preferably non-volatile in embodiments where the agents are impregnated into a solid porous materials. In some embodiments lysing agents are mixed together. Other materials may be mixed with the lysing agents to modify the lytic effects. Such exemplary materials may be, without limitation, buffers, salts, and proteins. In preferred embodiments lysing agents will be used in amounts that are in excess of the minimum amount required to lyse cells. In some embodiments lysing agents will be used that can lyse both white and red cells.

One of the advantages of the present invention is that any reagents necessary to perform an assay on a fluidic device according to the present invention are preferably on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

In a preferred embodiment there is at least one reagent chamber. In some embodiments there may be two, three, four, five, six, or more, or any number of reagent chambers as are necessary to fulfill the purposes of the invention. A reagent chamber is preferably in fluid communication with at least one reaction site, and when the fluidic device is actuated as described herein, reagents contained in said reagent chambers are released into the fluidic channels within the fluidic device.

Reagents according to the present invention include without limitation wash buffers, enzyme substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies, or other materials necessary to run an assay on a fluidic device. An enzyme conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments the reagents comprise immunoassay reagents.

In some embodiments a reagent chamber contains approximately about 50 µl to about 1 ml of fluid. In some embodiments the chamber may contain about 100 µl of fluid. The volume of liquid in a reagent chamber may vary depending on the type of assay being run or the sample of bodily fluid provided. In some embodiments the reagents are initially stored dry and liquified upon initiation of the assay being run on the fluidic device.

In a preferred embodiment there is at least one reagent chamber. In some embodiments there may be two, three, four, five, six, or more, or any number of reagent chambers as are necessary to fulfill the purposes of the invention. A reagent chamber is preferably in fluid communication with at least one reaction site, and when the fluidic device is actuated as described herein, reagents contained in said reagent chambers are released into the fluidic channels within the fluidic device.

Reagents according to the present invention include without limitation wash buffers, substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies or other materials necessary to run an assay on a fluidic device. An enzyme conjugate can be either a polyclonal antibody or monoclonal antibody labeled with an enzyme, such as alkaline phosphatase or horseradish peroxidase. In some embodiments the reagents are immunoassay reagents.

In some embodiments a reagent chamber contains approximately about 50 µl to about 1 ml of fluid. In some embodiments the chamber may contain about 100 µl of fluid. The volume of liquid in a reagent chamber may vary depending on the type of assay being run or the sample of bodily fluid provided. In some embodiments the reagents are initially stored dry and liquified upon initiation of the assay being run on the fluidic device.

Figure 5:
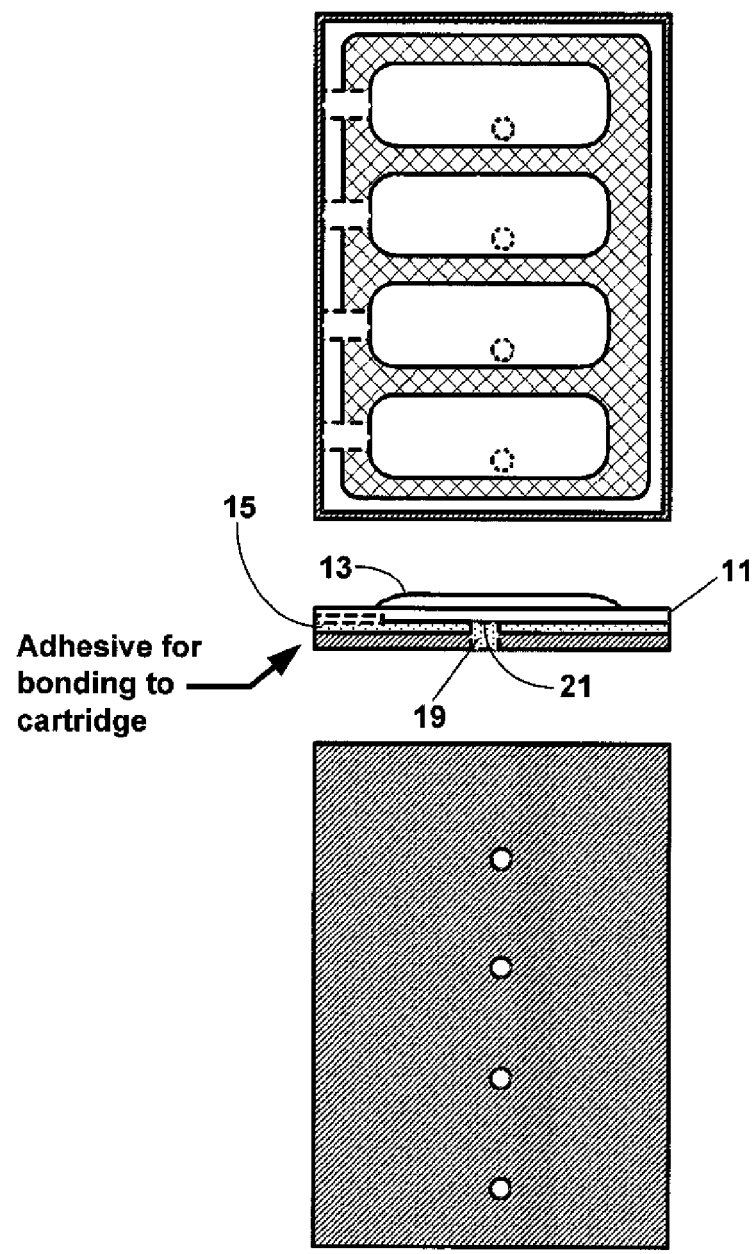
FIG. 5 shows a top, side, and bottom view of exemplary reagent chambers of the present invention.
Figure 6:
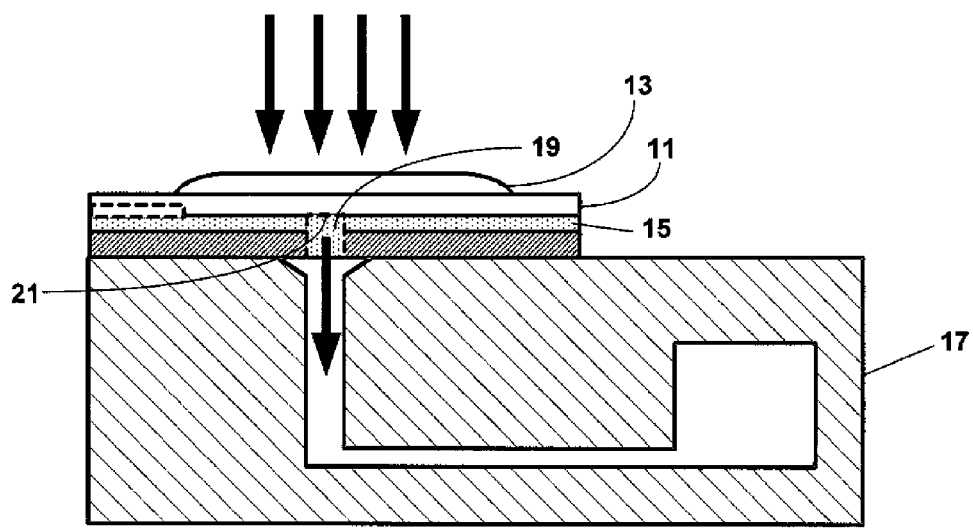
FIG. 6 illustrates an exemplary side view of a reagent chamber in fluidic communication with a fluidic device.

FIG. 5 illustrate a different embodiment of a sealed reagent chamber. FIG. 5 shows a top, side, and bottom view of a reagent chamber. A top layer 11 contains a plurality of bubbles or pouches 13. A bottom layer 15 has a bottom surface that is bonded to the fluidic device base 17 as shown in FIG. 6. The bottom layer 15 has a plurality of fluidic channels 19 dispersed through the entire surface, where each channel traverses the bottom layer 15. The fluid in the reagent chamber is contained within the chamber by pressure burstable seal 21 between the fluidic channel 19 and the chamber 13. The burstable seal 21 is designed such that at a predetermined pressure the seal bursts allowing the fluid in the chamber 13 to flow out into a fluidic channel 19.

Figure 7:
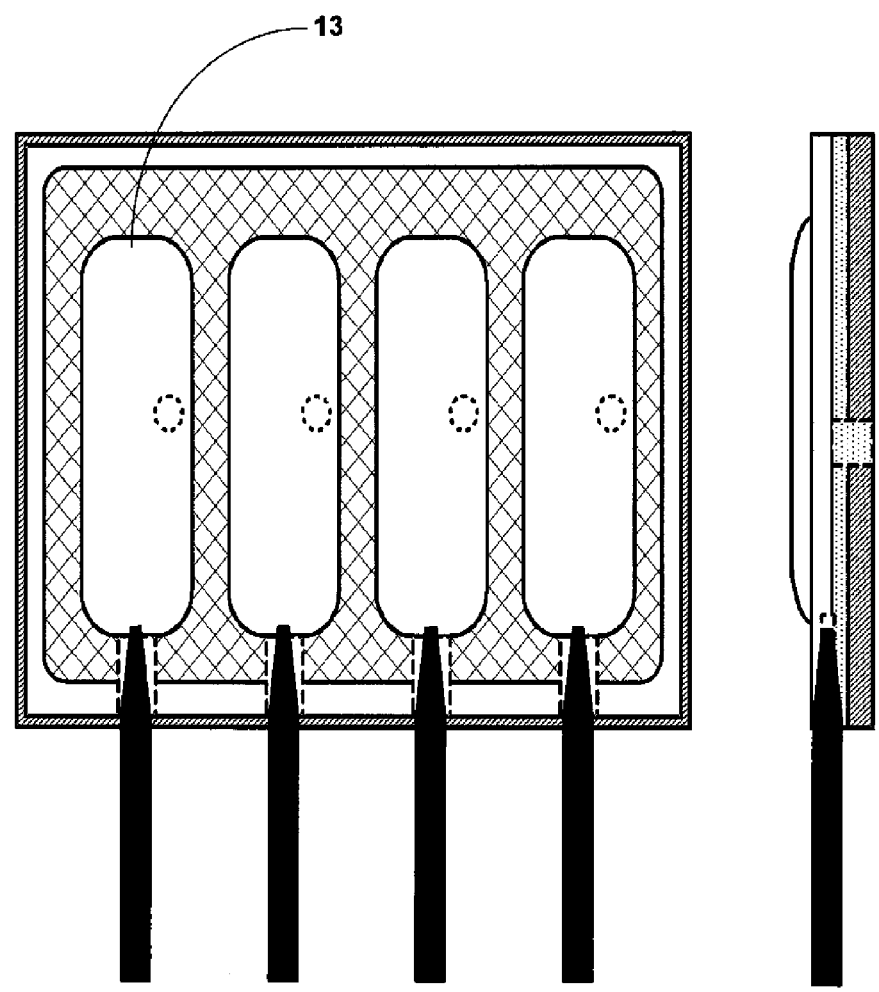
FIG. 7 illustrates exemplary reagent chambers being filled with reagents.

FIG. 7 shows an exemplary process of filling the reagent chambers 13 with, for example, reagents. Reagent chambers 13 may be filled with fluid using a fill channel and a vacuum draw channel. The process of filling the reagents involves first removing all the air from the chamber. This is done by drawing a vacuum through the vacuum draw channel. Once the vacuum is drawn, a permanent seal is placed between the fill channel and the vacuum draw channel. Next, required reagents are dispensed into the chamber through the fill channel. Then, a permanent seal is placed between the chamber and the fill channel. This ensures that when the chamber is compressed, the fluid can flow in only one direction, towards the burstable seal. If the compression imparts a pressure larger than the burst pressure of seal, the seal bursts and the fluid flows into the fluidic channel.

Figure 8:
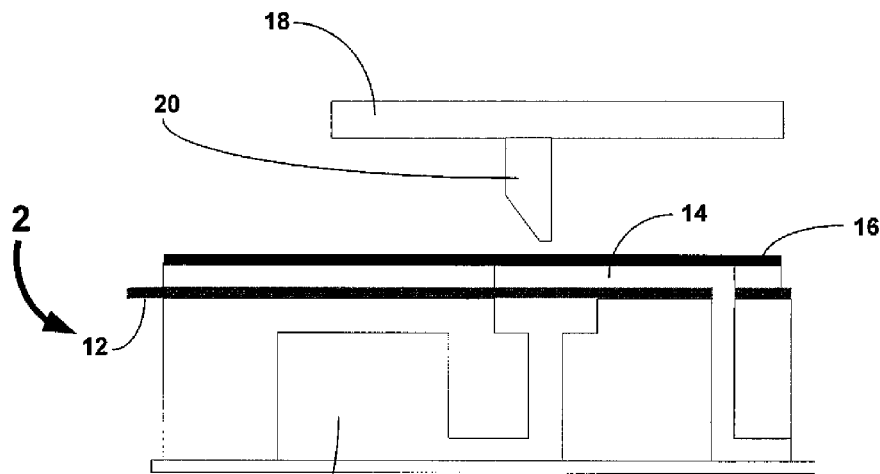
FIGS. 8 and 9 illustrate a side view of an exemplary fluidic device in combination with actuating elements of the reader assembly.
Figure 9:
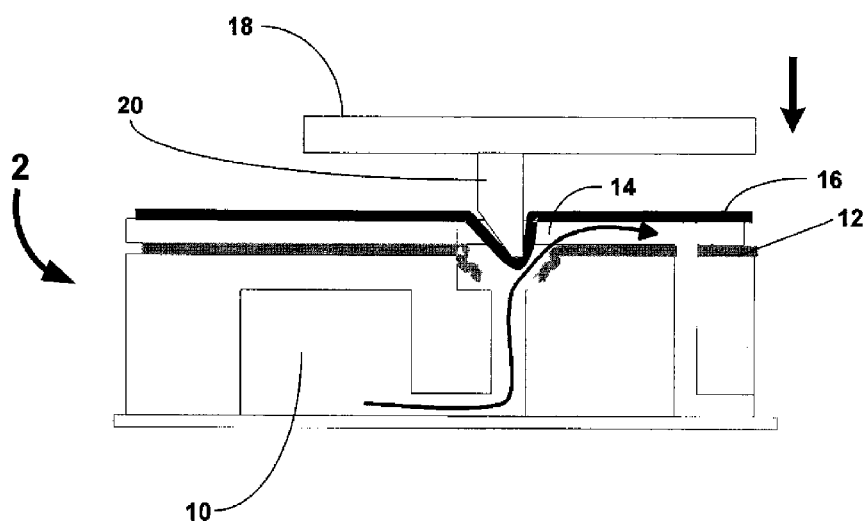

FIGS. 8 and 9 illustrate an embodiment of a fluidic device in operation with actuating elements as described herein. Fluidic device 2 contains a reagent chamber 10 and a layer of burstable foil 12 enclosing the reagent chamber. Above the burstable foil 12 is a portion of the microfluidic circuit 14. A tough, but elastomeric top cover 16 acts as the top layer of the fluidic device 2. The reader assembly includes a valve actuation plate 18. Securely attached to the plate 18 is a non-coring needle 20 such that when the plate is lowered, the sharp edge of the needle contacts the elastomeric cover 16. The top cover could also be made of flexible silicone material that would act as a moisture impermeable seal. This embodiment also provides a solution to liquid evaporation and leakage from a fluidic device by isolating any liquid reagents in the fluidic device from any dry reagents until the assay is initiated.

In preferred embodiments the reagent chamber and sample collection unit are fluidly connected to reaction sites where bound reactant can detect an analyte of interest in the bodily fluid sample using the assay. A reaction site could then provide a signal indicative of the presence of the analyte of interest, which can then be detected by a detection device described in detail herein below.

In some embodiments the reactions sites are flat but they may take on a variety of alternative surface configurations. The reaction site preferably forms a rigid support on which a reactant can be immobilized. The reaction site surface is also chosen to provide appropriate light-absorbing characteristics. For instance, the reaction site may be functionalized glass, Si, Ge, GaAs, GaP, Sift, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. Other appropriate materials may be used in accordance with the present invention.

A reactant immobilized at a reaction site can be anything useful for detecting an analyte of interest in a sample of bodily fluid. For instance, such reactants include without limitation nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or noncovalent, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art.

In some embodiments there are more than one reaction sites which can allow for detection of multiple analytes of interest from the same sample of bodily fluid. In some embodiments there are two, three, four, five, six, or more reaction sites, or any other number of reaction sites as may be necessary to carry out the intent of the invention.

In embodiments with multiple reaction sites on a fluidic device, each reaction site may contain a probe different from a probe on a different reaction site. In a fluidic device with, for example, three reaction sites, there may be three different probes, each bound to a different reaction site to bind to three different analytes of interest in the sample. In some embodiments there may be different probes bound to a single reaction site if, for example, a CCD with multiple detection areas were used as the detection device, such that multiple different analytes could be detected in a single reaction site. The capability to use multiple reaction sites in addition to multiple different probes on each reaction site enables the high-throughput characteristics of the present invention.

Figure 13A:
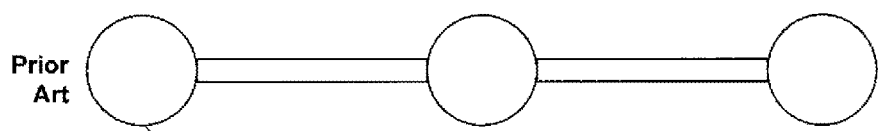
FIGS. 13A-D illustrate exemplary fluidic channels between reaction sites.
Figure 13B:
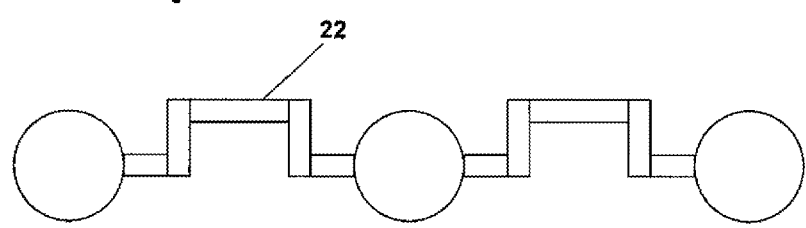
Figure 13C:
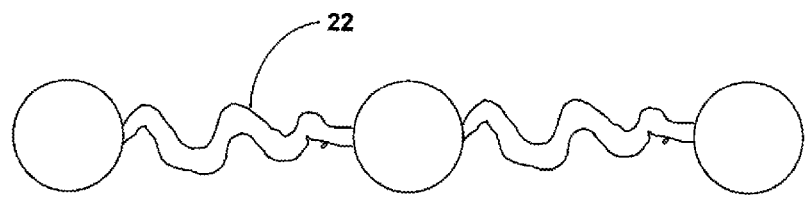
Figure 13D:
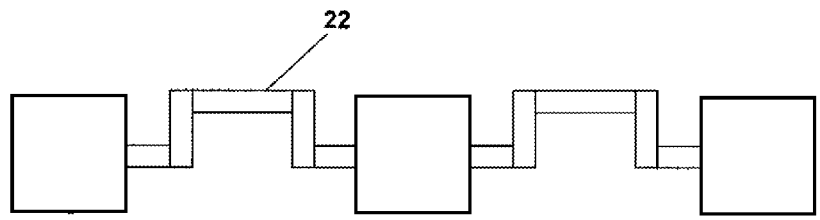

The present invention allows for the detection of multiple analytes on the same fluidic device. If assays with different luminescent intensities are run in adjacent reaction sites, photons (signals that emanate from the reactions) may travel from one reaction site to an adjacent reaction site, as reaction sites may be constructed of materials that allow photons to travel through the fluidic channels that connect the sites. This optical cross talk may compromise the accuracy of the detected photons. FIGS. 13B and 13C illustrate different embodiments of this invention that can eliminate or reduce the amount of optical cross-talk. Non-linear channels 22 will not allow photons (light) to pass through. Hence, embodiments such as those shown in FIGS. 13B and 13C would not allow signals from a reaction site to contaminate a signal produced from an adjacent site from which a detection device may be detecting. Additionally, the edges or walls of a reaction site may be constructed using optically opaque materials so that light will not escape the wells. In some embodiments the reaction sites are white or opaque.

In one exemplary configuration, the bound reactants in the at least one reaction site are localized around the center of said reaction site. In another exemplary configuration, an outer edge of the at least one reaction site is at a distance sufficiently far from said bound reactants to reduce signals unrelated to the presence of said analyte. Distancing the edge of the reaction site from the center area where bound reactants are concentrated allows reduction of interfering signals from the background that does not relate to the presence of the analyte of interest.

At least one of these channels will typically have small cross sectional dimensions. In some embodiments the dimensions are from about 0.01 mm to about 5 mm, preferably from about 0.03 mm to about 3 mm, and more preferably from about 0.05 mm to about 2 mm. Fluidic channels in the fluidic device may be created by, for example without limitation, precision injection molding, laser etching, or any other technique known in the art to carry out the intent of the invention.

Figure 15:
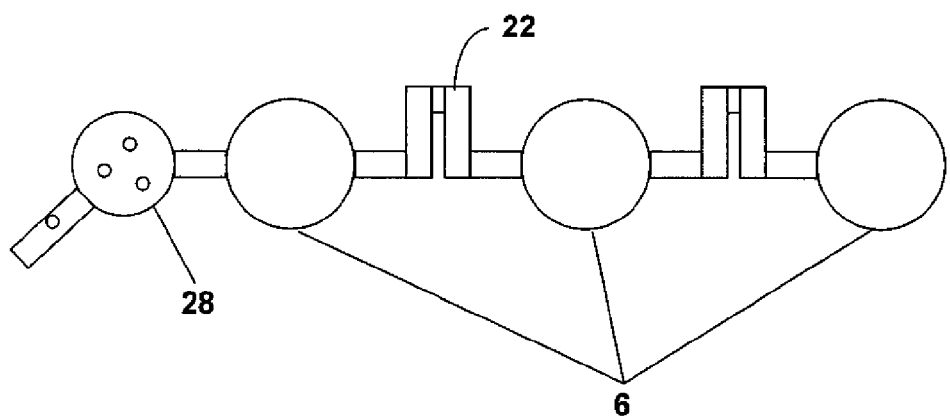
FIG. 15 shows an exemplary bubble trapper or remover to prevent bubbles from entering the reaction sites.

One of the common problems encountered in a microfluidic based assay system is the presence of air or gas bubbles. It is extremely difficult to remove a bubble once it is trapped within a fluidic channel. Bubbles present anywhere in the fluidic circuit, particularly in the reaction sites can compromise the assay capabilities. A bubble may end up occupying part of all of the surface area of a reaction site. Consequently the reader may end up reading a muted signal or no signal at all. FIG. 15 illustrates an embodiment where a bubble could be trapped in a filter 28 before it reaches a reaction site 6. A bubble trapper 28 can be positioned between a sample collection unit 4 and reaction site 6. The bubble trapper can have such a geometry that the bubbles tend to migrate towards the edges of this surface and remain stuck at that service, thereby not entering into the reaction sites.

Manufacturing of the fluidic channels may generally be carried out by any number of microfabrication techniques that are well known in the art. For example, lithographic techniques are optionally employed in fabricating, for example, glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding or stamp molding methods where large numbers of substrates are optionally produced using, for example, rolling stamps to produce large sheets of microscale substrates or polymer microcasting techniques where the substrate is polymerized within a micromachined mold.

In some embodiments at least one of the different layers of the fluidic device may be constructed of polymeric substrates. Non limiting examples of polymeric materials include polystyrene, polycarbonate, polypropylene, polydimethysiloxanes (PDMS), polyurethane, polyvinylchloride (PVC), and polysulfone.

The fluidic device may be manufactured by stamping, thermal bonding, adhesives or, in the case of certain substrates, for example, glass, or semi-rigid and non-rigid polymeric substrates, a natural adhesion between the two components. In some embodiments the fluidic device is manufactured by ultrasonic or acoustic welding.

FIG. 2 shows one embodiment of the invention in which fluidic device 2 is comprised of seven layers. Features as shown are, for example, cut in the polymeric substrate such that when the layers are properly positioned when assembly will form a fluidic network. In some embodiments more or fewer layers may be used to construct a fluidic device to carry out the purpose of the invention.

One goal of the present invention is to prevent fluid inside a fluidic device from contacting the components of a reader assembly which may need to remain dry and or uncontaminated, and also to prevent contamination to a detection device within the reader assembly. A leak in the fluidic device could result in liquids, for example reagents or waste, escaping from the fluidic device and contaminating the reader. In other embodiments a liquid absorbing material, such as polymeric materials found in diapers, could be placed within a portion of the fluidic channel or waste chamber to absorb the waste liquid. A non-limiting example of such a polymer is sodium polyacrylate. Such polymers can absorb fluids hundreds of times their weight. Hence, only minute quantities of such polymeric materials may be required to accomplish the goal of absorbing leaked fluids. In some embodiments a waste chamber is filled with a superabsorbent material. In some embodiments leaked liquid may be converted into a gel or other solid or semi-solid form.

FIGS. 8 and 9 illustrate an exemplary sequence to initiate the flow of a reagent within the fluidic device. An actuation plate 18 in the reader assembly comprises a non-coring needle or pin 20 which when lowered flexes the top cover 16, as it is preferably made of strong, flexible elastomeric material. However, the easily rupturable foil 12 then ruptures due to the stress induced by the flexing of top cover 16. Valves located downstream to the reagent chamber puncture different areas of foil in the fluidic device and can then work in tandem with a pump in the reader assembly to create a vacuum force to pull the reagent out of the reagent chamber 6 into a fluidic channel and then direct the flow of the reagent to a reaction site. At least one valve is preferably fluidically connected to a pump housed within the reader assembly. The non-coring needle or pin 20 is removed from the fluidic device when the device is removed from the reader assembly. One of the advantages of this embodiment is that no on-chip pump is required, which, at least, decreases the size and cost of the fluidic device, and allows the device to be disposable.

In some embodiments a method of manufacturing a fluidic device for detecting an analyte in a biological fluid of a subject comprises providing a plurality of layers of a material, wherein at least one of said layers comprises a sample collection unit, wherein at least one of said layers comprises a filtration site, wherein at least one of said layers comprises a reactant chamber, wherein at least one of said layers comprises a fluidic channel, wherein at least one of said layers comprises a reaction site, wherein at least one of said layers comprises a waste chamber; and ultrasonically welding said layers together such that a fluidic network of channels exists between said sample collection unit, said reactant chambers, said filtration site, said reaction sites, said fluidic channel, and said waste chamber.

In preferred embodiments the different layers of the fluidic device are ultrasonically welded together according to methods known in the art. The layers may also be coupled together using other methods, including without limitation stamping, thermal bonding, adhesives or, in the case of certain substrates, for example, glass, or semi-rigid and non-rigid polymeric substrates, a natural adhesion between the two components The subject system provides an effective means for high throughput and real-time detection of analytes present in a bodily fluid from a subject. The detection methods may be used in a wide variety of circumstances including identification and quantification of analytes that are associated with specific biological processes, physiological conditions, disorders or stages of disorders. As such, the subject apparatus and systems have a broad spectrum of utility in, e.g. drug screening, disease diagnosis, phylogenetic classification, parental and forensic identification. The subject apparatus and systems are also particularly useful for advancing preclinical and clinical stage of development of therapeutics, improving patient compliance, monitoring ADRs associated with a prescribed drug, and developing individualized medicine.

As used herein, the term "subject" or "patient" is used interchangeably herein, which refers to a vertebrate, preferably a mammal, more preferably a human. Mammals include, but are not limited to, murines, simians, humans, farm animals, sport animals, and pets.

In some embodiments a sample of bodily fluid can first be provided to the fluidic device by any of the methods described herein. The fluidic device can then be inserted into the reader assembly. An identification detector housed within the reader assembly can detect an identifier of the fluidic device and communicate the identifier to a communication assembly, which is preferably housed within the reader assembly. The communication assembly then transmits the identifier to an external device which transmits a protocol to run on the fluidic device based on the identifier to the communication assembly. A controller preferably housed within the reader assembly controls actuating elements including at least one pump and one valve which interact with the fluidic device to control and direct fluid movement within the device. In some embodiments the first step of the assay is a wash cycle where all the surfaces within the fluidic device are wetted using a wash buffer. The fluidic device is then calibrated using a calibration assembly by running the same reagents as will be used in the assay through the calibration reaction sites, and then a luminescence signal from the reactions sites is detected by the detection means, and the signal is used in calibrating the fluidic device. The sample containing the analyte is introduced into the fluidic channel. The sample may be diluted and further separated into plasma or other desired component at a filter. The separated sample now flows through the reaction sites and analytes present therein will bind to reactants bound thereon. The plasma of sample fluid is then flushed out of the reaction wells into a waste chamber. Depending on the assay being run, appropriate reagents are directed through the reaction sites to carry out the assay. All the wash buffers and other reagents used in the various steps, including the calibration step, are collected in wash tanks. The signal produced in the reaction sites is then detected by any of the methods described herein.

The term "analytes" according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, biomarker, gene, protein, or hormone, or any combination thereof. At a molecular level, the analytes can be polypeptide glycoprotein, polysaccharide, lipid, nucleic acid, and a combination thereof.

Of particular interest are biomarkers are associated with a particular disease or with a specific disease stage. Such analytes include but are not limited to those associated with autoimmune diseases, obesity, hypertension, diabetes, neuronal and/or muscular degenerative diseases, cardiac diseases, endocrine disorders, any combinations thereof.

Of also interest are biomarkers that are present in varying abundance in one or more of the body tissues (i.e., tissue-specific) including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are analytes that are indicative of a microorganism. Exemplary microorganisms include but are not limited to bacterium, virus, fungus and protozoa. Analytes that can be detected by the subject method also include blood-born pathogens selected from a non-limiting group that consists of *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans*.

Analytes that can be detected by the subject method also encompass a variety of sexually transmitted diseases selected from the following: gonorrhea (*Neisseria gorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional analytes that can be detected by the subject methods encompass a diversity of respiratory pathogens including but not limited to *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*.

A variety of assays may be performed on a fluidic device according to the present invention to detect an analyte of interest in a sample. A wide diversity of labels are available in the art that can be employed for conducting the subject assays. In some embodiments labels are detectable by spectroscopic, photochemical, biochemical, immunochemical, or chemical means. For example, useful nucleic acid labels include 32P, 35S, fluorescent dyes, electron-dense reagents, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, bioluminescent labels, calorimetric labels, or magnetic particles. Labeling agents optionally include, for example, monoclonal antibodies, polyclonal antibodies, proteins, or other polymers such as affinity matrices, carbohydrates or lipids. Detection proceeds by any of a variety of known methods, including spectrophotometric or optical tracking of radioactive or fluorescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Thus, a label includes without limitation any composition detectable by spectroscopic, photochemical, biochemical, immunochemical, electrical, optical thermal, or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti-ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6, 7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In some embodiments immunoassays are run on the fluidic device. While competitive binding assays, which are well known in the art, may be run in some embodiments, in preferred embodiments a two-step method is used which eliminates the need to mix a conjugate and a sample before exposing the mixture to an antibody, which may be desirable when very small volumes of sample and conjugate are used, as in the fluidic device of the present invention. A two-step assay has additional advantages over the competitive binding assays when use with a fluidic device as described herein. It combines the ease of use and high sensitivity of a sandwich (competitive binding) immunoassay with the ability to assay small molecules.

Figure 10:
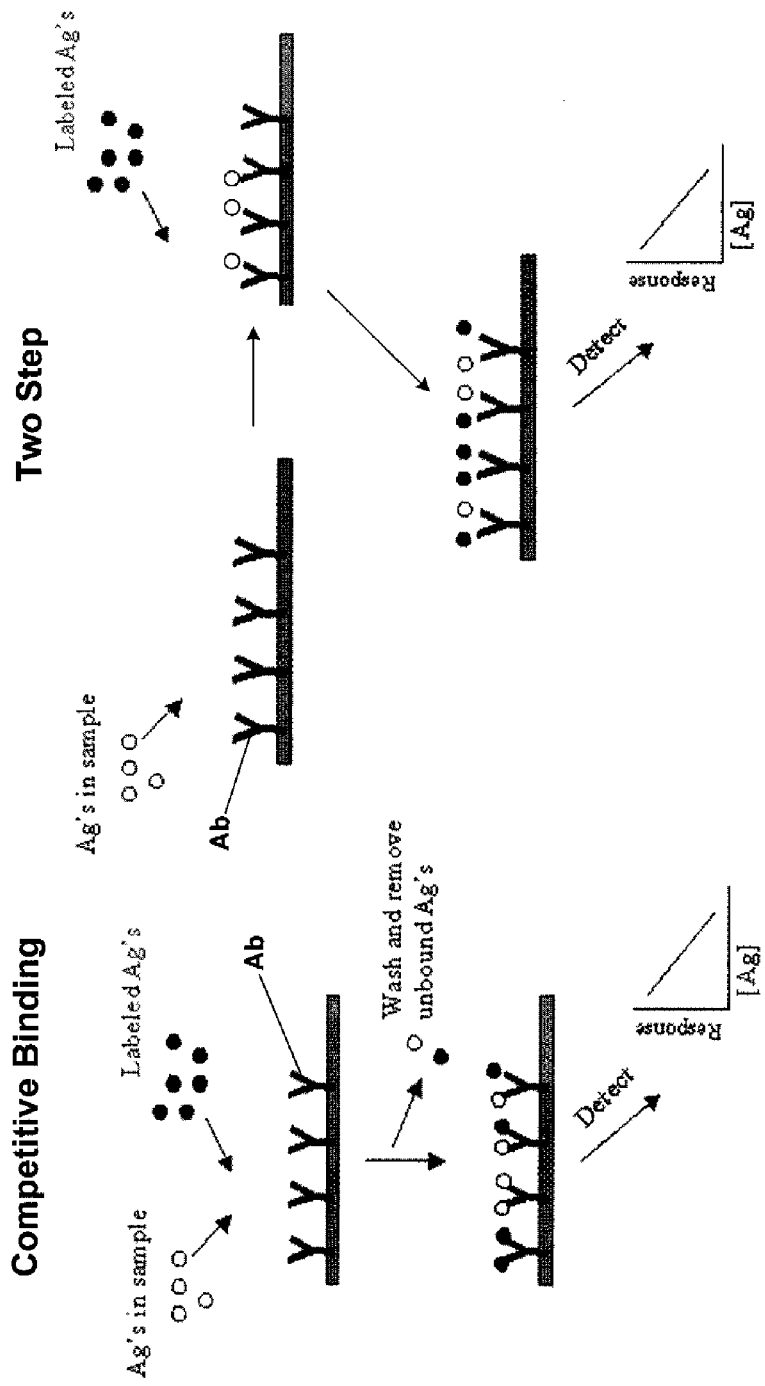
FIG. 10 illustrates a two-step assay and a competitive binding assay.

In an exemplary two-step assay shown in FIG. 10, the sample containing analyte ("Ag") first flows over a reaction site containing antibodies ("Ab"). The antibodies bind the analyte present in the sample. After the sample passes over the surface, a solution with analyte conjugated to a marker ("labeled Ag") at a high concentration is passed over the surface. The conjugate saturates any of the antibodies that have not yet bound the analyte. Before equilibrium is reached and any displacement of pre-bound unlabelled analyte occurs, the high-concentration conjugate solution is washed off. The amount of conjugate bound to the surface is then measured by the appropriate technique, and the detected conjugate is inversely proportional to the amount of analyte present in the sample.

Figure 11:
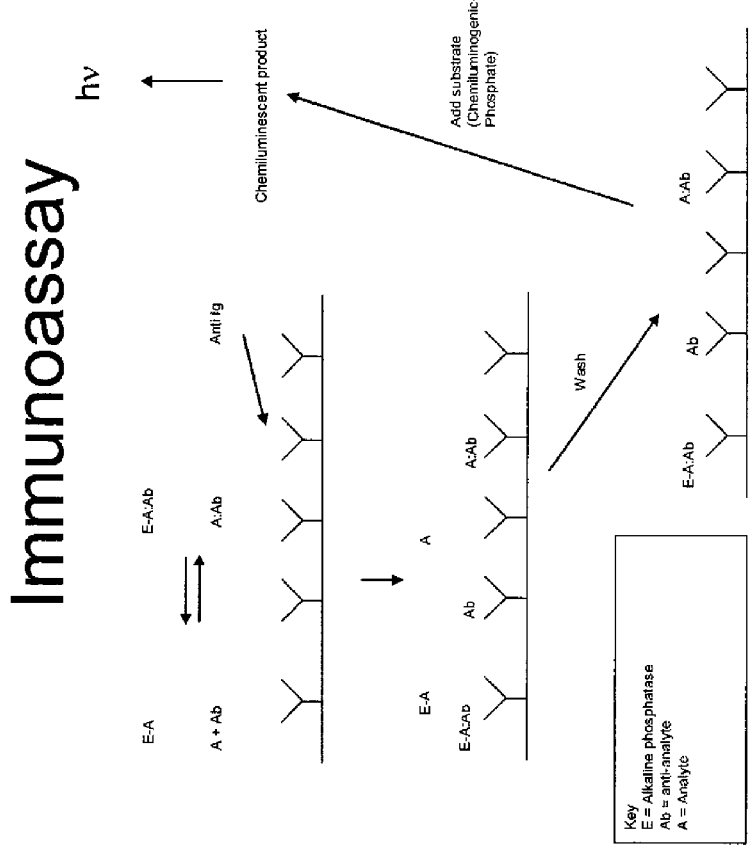
FIG. 11 shows an exemplary two-step chemiluminescence enzyme immunoassay.
Figure 12:
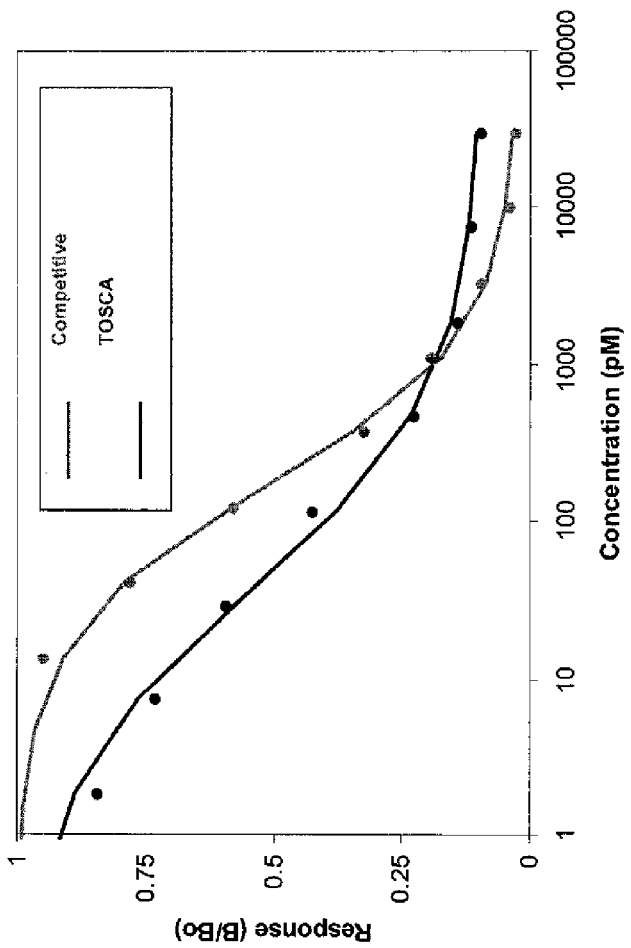
FIG. 12 illustrates the increased sensitivity of the two-step chemiluminescence enzyme immunoassay.

An exemplary measuring technique for a two-step assay is a chemiluminescence enzyme immunoassay as shown in FIG. 11. As is known in the field, the marker can be a commercially available marker such as dioxitane-phosphate, which is not luminescent but becomes luminescent after hydrolysis by, for example, alkaline phosphatase. An enzyme such as alkaline phosphatase is also passed over the substrate to cause the marker to luminesce. In some embodiments the substrate solution is supplemented with enhancing agents such as, without limitation, fluorescein in mixed micelles, soluble polymers, or PVC which create a much brighter signal than the luminophore alone. Moreover, an alkaline phosphatase conjugate with a higher turnover number than that used in the commercial assay is employed. This allows signal generation to proceed much more rapidly and a higher overall signal is achieved. The increased sensitivity of the two-step chemiluminescent enzyme immunoassay (TOSCA) is illustrated in FIG. 12. FIG. 12 shows that for analytes in the picomolar concentration, TOSCA is able to provide a more robust signal (higher sensitivity) than a competitive binding assay. Use of a two-step binding assay thus contributes to higher sensitivity capabilities of the present invention.

Figure 14A:
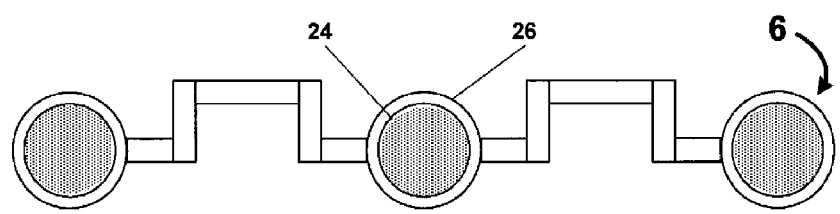
FIGS. 14A and 14B illustrate reaction sites to reduce the signal from unbound conjugates remaining in reaction sites.
Figure 14B:
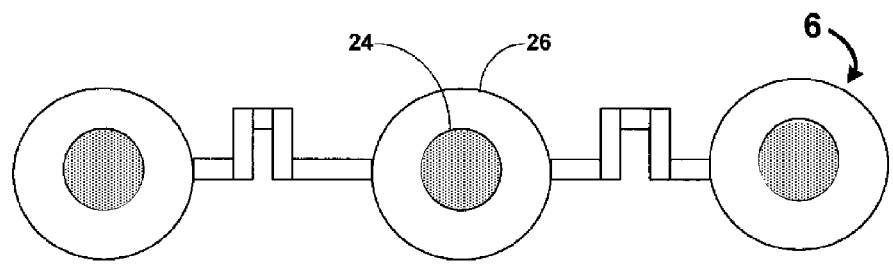

In some embodiments, unbound conjugates may need to be washed from a reaction site to prevent unbound conjugates from activating the substrate and producing and inaccurate signal. It may be difficult to remove conjugates sticking to the edges of the reaction sites in such a fluidic device if, for example, there is not an excess of a wash solution. To decrease the signal contributed from unbound conjugates stuck to the edge of a reaction site, it may be advantageous to expand the reaction site edge or wall radius in order to distance stuck conjugate from the desired actual detection area, represented by bound probes. FIGS. 14A and 14B illustrates this concept. Reaction site 6 contains reaction surface 24 and edge or wall surface 26. An edge surface 26 is shown at a greater distance from the center of the reaction site 6 than is the edge surface of the prior art design. This allows unbound conjugates to adhere to the edge surfaces and be distanced from bound conjugates, which are concentrated closer to the center of the reaction site 6.

In preferred embodiments of the invention the fluidic device includes at least one waste chamber to trap or capture all liquids after they have been used in the assay. In preferred embodiments, there is more than one waste chamber, at least one of which is to be used with a calibration assembly described herein below. On-board waste chambers also allow the device to be easily disposable. The waste chamber is preferably in fluidic communication with at least one reaction site.

The subject system is capable of detecting a plurality of analytes. In one aspect, the system can be used to identify and quantify analytes present varying concentrations that differ by more than 3 orders of magnitude.

What is claimed is:

1. An apparatus comprising:
a plurality of adjacent reaction sites;
a sample collection unit, for introducing a biological fluid, in fluid communication with the plurality of adjacent reaction sites;
a plurality of reagent chambers, including a plurality of reagents, in fluid communication with said reaction sites,
wherein each of said plurality of reaction sites comprise one or more reactants bound thereto for detecting an analyte; and
a system of fluidic channels to allow said biological fluid and said plurality of reagents to flow in said apparatus;
wherein at least one of said plurality of adjacent reaction sites is between two optical barriers, said two optical barriers comprise two non-linear channels configured to not allow photons to pass through the two non-linear channels and contaminate signals produced from the plurality of adjacent reaction sites;
walls of the at least one reaction site comprise optically opaque materials so that light will not escape said at least one reaction site through said walls, and
the two nonlinear channels provide fluid communication between the plurality of adjacent reaction sites.

2. The apparatus of claim 1, further comprising a plurality of waste chambers in fluid communication with at least one of said adjacent reaction sites.

3. The apparatus of claim 1 wherein each of said non-linear channels located between said plurality of adjacent reaction sites is configured as an optical barrier defining a fluid pathway with at least three bends between said adjacent reaction sites.

4. The apparatus of claim 1 wherein the sample collection unit is sized to contain biological fluid that is less than about 500 microliters.

5. The apparatus of claim 1 wherein said reaction sites comprise walls of a white opaque material.

6. The apparatus of claim 1, wherein the plurality of reagents comprise immunoassay reagents.

7. The apparatus of claim 6, wherein said plurality of reagents are configured to react to detect a plurality of different analytes.

8. The apparatus of claim 6, wherein the immunoassay reagents configured to react to detect a polypeptide glycoprotein, polysaccharide, lipid, nucleic acid, and a combination thereof.

9. The apparatus of claim 6, wherein the immunoassay reagents are configured to react to detect a member selected from the group consisting of drug, drug metabolite, biomarker indicative of a disease, tissue specific marker, and biomarker specific for a cell or cell type.

10. The apparatus of claim 1 wherein said at least one of said reaction sites is fluidically coupled by a) at least a first of said non-linear channels to another of said reaction sites and b) at least a second of said non-linear channels to yet another of said reaction sites.

11. The apparatus of claim 1 wherein at least one of said non-linear channels defines a path comprising a plurality of serpentine turns.

12. The apparatus of claim 1 wherein at least one of said non-linear channels defines a path comprising a plurality of repeating turns.

13. An apparatus comprising
a plurality of adjacent reaction sites;
a sample collection unit, for introducing a biological fluid, in fluid communication with the plurality of adjacent reaction sites, wherein said plurality of adjacent reaction sites comprise a plurality of bound reactants for detecting an analyte;
a plurality of reagent chambers, including a plurality of reagents, in fluid communication with said adjacent reaction sites; and
a system of fluidic channels to allow said biological fluid and said plurality of reagents to flow in said apparatus;
wherein at least one of said plurality of adjacent reaction sites is between two optical barriers, said two optical barriers comprise two non-linear channels configured to not allow photons to pass through the two non-linear channels and contaminate signals produced from the plurality of adjacent reaction sites;
a wall of the at least one reaction site comprises an optically opaque material so that light will not escape said at least one reaction site through said walls, and
the two nonlinear channels provide fluid communication between the plurality of adjacent reaction sites;
wherein at least one of said adjacent reaction sites comprises a reaction surface with bound reactants around a center of the at least one reaction site and said bound reactants are spaced apart from said wall of the at least one reaction site by a concentric ring-shaped area, said at least one reaction site configured to reduce signal from any unbound conjugates remaining in the at least one reaction site.

14. The apparatus of claim 13, wherein said bound reactants in the at least one reaction site are concentrated at the center of said reaction site relative to quantities at an outer edge of said at least one reaction site.

15. The apparatus of claim 14, wherein an outer edge of the at least one reaction site is at a distance from said bound reactants at said center to reduce signals from unbound conjugates unrelated to the presence of said analyte.

16. The apparatus of claim 13, further comprising a waste chamber in fluid communication with at least two of said adjacent reaction sites.

17. The apparatus of claim 13 wherein said at least one of said reaction sites is fluidically coupled by a) at least a first of said non-linear channels to another of said reaction sites and b) at least a second of said non-linear channels to yet another of said reaction sites.

* * * * *